United States Patent [19]

Schuster

[11] Patent Number: 4,847,394

[45] Date of Patent: Jul. 11, 1989

[54] PREPARATION OF 2,2-DI-[LYCIDYLOXYCYCLOHEXYL]-PROPANE

[75] Inventor: Ludwig Schuster, Limburgerhof, Fed. Rep. of Germany

[73] Assignee: BASF Aktiengesellschaft, Ludwigshafen, Fed. Rep. of Germany

[21] Appl. No.: 82,126

[22] Filed: Aug. 6, 1987

[30] Foreign Application Priority Data

Aug. 30, 1986 [DE] Fed. Rep. of Germany ....... 3629632

[51] Int. Cl.$^4$ ............................................. C07C 301/00
[52] U.S. Cl. ................................................... 549/540
[58] Field of Search ......................................... 549/540

[56] References Cited

U.S. PATENT DOCUMENTS

| | | | |
|---|---|---|---|
| 2,943,095 | 6/1960 | Farnham et al. | 549/517 |
| 3,336,241 | 8/1967 | Shokal | 549/540 |
| 4,459,419 | 7/1984 | Seemuth | 549/356 |
| 4,626,544 | 12/1986 | Schulz et al. | 514/383 |

FOREIGN PATENT DOCUMENTS 828776 12/1969 Canada .
2132547 6/1971 Fed. Rep. of Germany ...... 549/356

OTHER PUBLICATIONS

Chem. Abst., vol. 82, No. 16, p. 52:99079K.
European Search Report EP 87 11 2316.
D. Ahragam and Y. Deux, Comptes Rendus, vol. 205, pp. 285–286 (1937).
Houben-Weyl, vol. 6/3 (1965), p. 445.

*Primary Examiner*—Glennon H. Hollrah
*Assistant Examiner*—Raymond Covington
*Attorney, Agent, or Firm*—Keil & Weinkauf

[57] ABSTRACT

2,2-di-[p-glycidyloxycyclohexyl]-propane is prepared by catalytic hydrogenation by a process in which 2,2-di-[p-glycidyloxyphenyl]-propane is hydrogenated in the presence of a ruthenium catalyst at 20°–60° C. and under a pressure above 100 bar.

4 Claims, No Drawings

PREPARATION OF 2,2-DI-[LYCIDYLOXYCYCLOHEXYL]-PROPANE

The catalytic hydrogenation of the oxirane ring takes place very readily. For example, the hydrogenation of 1,2-epoxy-1-phenylbutene gives 1-phenylbutanol (D. Ahragam and Y. Deux, C. r. 205 (1937), 285). Similarly, in the hydrogenation of epoxide compounds which additionally carry an aromatic nucleus, it is invariably only the oxirane ring which is cleaved with alcohol formation; the benzene ring is not attacked (Houben-Weyl, volume 6/3, page 445).

We have found that 2,2-di-[p-glycidyloxycyclohexyl]-propane is obtained by catalytic hydrogenation in a form which can be directly further processed, if 2,2-di-[p-glycidyloxyphenyl]-propane is hydrogenated in the presence of a ruthenium catalyst at 20°–60° C. and under a pressure above 100 bar.

In the catalytic hydrogenation of the bisglycidyl ether of 2,2-dihydroxydiphenylpropane, ie. of bisphenol A, over a ruthenium catalyst, it is surprising that, in contrast to the known scheme, it is not the oxirane rings but the two aromatic rings which are saturated, the corresponding dicyclohexane compound being formed.

Ruthenium on an inert carrier, such as active carbon, or, preferably, on the oxide hydrate obtained by precipitation from an aqueous solution of ruthenium trichloride, can be used as the catalyst for the hydrogenation.

The amount of hydrogenation catalyst used depends to a slight extent on the purity of the starting material. In general, the catalyst concentration in the hydrogenation mixture should be from 1 to 3 parts by weight of ruthenium per 1,000 parts by weight of bisglycidyl ether.

It is advantageous to isolate the noble metal catalyst when the reaction is complete and to reuse it. If impurities in the starting material, principally chlorine (either covalently bonded or as chloride), poison the catalyst and thus make it impossible to reuse it, working up by a conventional method, for example via ruthenium tetroxide, is advisable.

The hydrogenation is carried out under a pressure above 100 bar, in general from 200 to 325 bar.

It is advantageous to carry out the hydrogenation in solution. Preferably used solvents are ethers, such as methyl tert-butyl ether or glycol dimethyl ether; tetrahydrofuran and dioxane have proven particularly advantageous. Very highly concentrated solutions can be used, for example a 55% strength solution in tetrahydrofuran.

The reaction temperature should be chosen within relatively narrow limits. Thus, the oxirane rings are cleaved at elevated temperatures, whereas at excessively low temperatures the aromatic systems are not yet saturated. The optimum temperature range for the selective hydrogenation of the nucleus is from 20° to 60° C., preferably from 40° to 50° C.

2,2-di-[p-glycidyloxycyclohexyl]-propane is a starting material or component of epoxy resin systems.

EXAMPLE 1.2 kg of bisphenol diglycidyl ether are dissolved in 1.1 l of tetrahydrofuran in an autoclave which has a capacity of 3.5 l and is provided with a magnetic stirrer. 10 g of a ruthenium oxide hydrate paste containing 1.4 g of ruthenium are added to this solution. The hydrogenation is carried out under 300 bar at 50° C. The total hydrogen absorption takes 10 hours.

The discharged hydrogenation mixture is filtered over bleaching earth and active carbon, and the filtrate is evaporated down.

The crude product thus obtained can be directly further processed. A particularly pure and pale product is obtained by distillation under reduced pressure. Under 0.1 mbar, the compound distills over at from 160° to 180° C.

I claim:

1. A process for the preparation of 2,2-di-[p-glycidyloxycyclohexyl]-propane by catalytic hydrogenation, wherein 2,2-di-[p-glycidyloxyphenyl]-propane is hydrogenated in the presence of a ruthenium catalyst at 20°–60° C. and under a pressure above 100 bar.

2. The process of claim 1, wherein the pressure is from 200 to 325 bar.

3. The process of claim 1, wherein the amount of ruthenium catalyst is from 1 to 3 parts by weight per 1,000 parts by weight of 2,2-di-[p-glycidyloxycyclophenyl]-propane.

4. The process of claim 1, wherein the catalyst is a ruthenium oxide hydrate paste.